US012678069B2

(12) United States Patent
Goldman et al.

(10) Patent No.: US 12,678,069 B2
(45) Date of Patent: Jul. 14, 2026

(54) METHOD AND APPARATUS FOR THREE-DIMENSIONAL MEASUREMENTS OF THE OUTER EAR SHAPE

(71) Applicant: Aurality, Inc., Herndon, VA (US)

(72) Inventors: Sigrid Smitt Goldman, Great Falls, VA (US); Mathieu Aubailly, Herndon, VA (US)

(73) Assignee: Aurality, Inc.

( * ) Notice: Subject to any disclaimer, the term of this patent is extended or adjusted under 35 U.S.C. 154(b) by 349 days.

(21) Appl. No.: 18/475,762

(22) Filed: Sep. 27, 2023

(65) Prior Publication Data

US 2025/0098982 A1     Mar. 27, 2025

(51) Int. Cl.
| | |
|---|---|
| *A61B 5/107* | (2006.01) |
| *A61B 5/00* | (2006.01) |
| *G06T 1/00* | (2006.01) |

(52) U.S. Cl.
CPC .......... *A61B 5/1075* (2013.01); *A61B 5/7405* (2013.01); *A61B 5/742* (2013.01); *A61B 5/7455* (2013.01); *A61B 5/748* (2013.01); *G06T 1/0007* (2013.01); *A61B 2560/02* (2013.01); *G06T 2207/30196* (2013.01)

(58) Field of Classification Search
USPC ......................................................... 358/131
See application file for complete search history.

(56) References Cited

U.S. PATENT DOCUMENTS

| | | | | |
|---|---|---|---|---|
| 8,032,337 | B2 * | 10/2011 | Deichmann .......... | H04R 1/1016 |
| | | | | 703/2 |
| 2014/0343900 | A1 * | 11/2014 | Goldstein ............... | G06F 30/00 |
| | | | | 703/1 |
| 2019/0293414 | A1 * | 9/2019 | Sorimoto ................. | G01B 9/02 |
| 2023/0126960 | A1 * | 4/2023 | Ogino .................. | H04N 23/675 |
| | | | | 348/78 |
| 2023/0200681 | A1 * | 6/2023 | Tanaka ............... | G01B 11/2518 |
| | | | | 356/601 |

* cited by examiner

*Primary Examiner* — Jacky X Zheng
(74) *Attorney, Agent, or Firm* — Sage Patent Group

(57)     ABSTRACT

A method, apparatus, and system for three-dimensional measurements of the outer ear shape, including the auditory canal and the concha. The apparatus may include a handpiece providing an earpiece dimensioned and shaped to occupy the auditory canal. The earpiece projects pattern lights, that can be selectively modulated onto an ear surface. The earpiece also provides flood illuminators and wide field-of-view imagers for capturing images generated by the projected light patterns. The handpiece provides a user interface for receiving one or more feedback modalities indicative of the location of a tip of the earpiece within the ear. A control unit located in the handpiece and a processing unit allow forming the three-dimensional measurements and their associated visualization.

6 Claims, 5 Drawing Sheets

METHOD AND APPARATUS FOR THREE-DIMENSIONAL MEASUREMENTS OF THE OUTER EAR SHAPE

BACKGROUND OF THE INVENTION

The present invention relates to the field of audiology and, more particularly, a method and apparatus for three-dimensional measurements of the outer ear shape, including the auditory canal and the concha. These measurements are fundamental to the design and subsequent manufacturing of hearing aids, hearing protections, and ear buds or ear bud adapters that are customized to the ear of a patient. The more accurate the measurements, the more effective and comfortable the ear device is.

Traditionally, audiologists achieve these measurements by conducting a physical impression of the ear using silicon material. The silicon material is first injected in a viscous state into the auditory canal and the concha of the patient to conform to the shape of the ear. The material then hardens in place for several minutes hence forming an impression of the ear shape. Finally, the hardened impression is extracted from the ear. These steps make the traditional impression process time consuming, costly, inaccurate, uncomfortable to the patient and they may be unsafe for the patient's ear drum. Time consuming since the silicon material needs to be injected, allowed to harden, and then extracted from the ear. Costly since the process requires consumable material for each impression of each patient. Inaccurate since the process of injecting a viscous material into a cavity consisting of soft tissue causes expansion of the cavity and is inherently inaccurate. Uncomfortable for the patient since injecting material and then extracting it from the ear is uncomfortable for the patient. Potentially unsafe since the impression material may contact the patient's ear drum as it is injected, while it hardens or while it is extracted by the audiologist.

In addition to the traditional method based on the use of impression material, there are three other existing technologies for capturing the shape of the ear. The first is based on inflatable membrane. This technology involves an inflatable membrane which is inserted into the ear canal in its deflated form and then inflated using a fluid (absorbing medium) to conform to the shape of the ear. The shape of the interior of the membrane is then measured through optical means and digital processing. This technology presents severe limitations, such as the following: costly, as each inflatable membrane is for single use; complex, as the technology requires a system (e.g., reservoir and tubing) for handling the fluid used to inflate and deflate the membrane—for the technology to function the fluid needs to maintain purity and be devoid of air or other gas, and managing these requirements increases the complexity of the system; inaccurate as the process of inflating the membrane inside the ear canal involves deformation of the ear canal surface (soft tissue) hence resulting in inaccurate measurements; and uncomfortable for the patient as inflating a device inside the ear canal can be uncomfortable for the patient.

The second alternative technology is based on the combination of an optical in-ear probe and target tracking. This approach combines several elements: (1) a narrow optical probe that is inserted into the ear canal and moved around the concha for capturing cross-section measurements of the ear; (2) tracking targets that are positioned around the ear of the patient for the duration of the scan; and (3) tracking sensors on the handpiece that track the tracking targets which are used to derive the position of the probe relative to the head of the patient through digital computation. This technology presents severe limitations, such as the following: complex, as the system includes tracking targets that need to be affixed to the head of the patient during the scanning process, making the system complex to operate, and it also requires periodic calibration; inaccurate, as the tracking targets that are affixed to the patient's head may move slightly while the operator is conducting the scan. This makes this solution prone to inaccurate outcomes.

The third existing technology is based on existing digital ear impressions stored on a remote server, which involves the following: (1) retrieving a series of video frames of a patient's ear; (2) transferring the series of frame to a remote server; and (3) reconstructing a 3D model of the ear on the remote server based on existing 3D digital ear impressions stored on the server. This technology is limited in the following ways: inaccurate, as the shape of the patient's ear is not directly measured or reconstructed rather ear landmarks are measured from the video frames, then measured 3D data points are compared with existing ear impressions stored on the server, and finally the shape of the ear is extrapolated; and complex, as the system requires a library of 3D ear digital impressions that were previously captured from other patients.

As can be seen, there is a need for an improved method and apparatus for three-dimensional measurements of the outer ear shape, including the auditory canal and the concha.

SUMMARY OF THE INVENTION

The present invention is based on an optical imaging system and enables capturing an impression of the ear without involving silicon material and its associated drawbacks while speeding up the process and yielding more accurate measurements. The invention maybe also be used for applications outside of the audiology field, for instance for measuring small cavities (e.g., other medical fields, mechanical inspection, metrology).

The present invention may include a method of measuring the 3D shape of the outer ear using the combination of a projector that projects a light pattern onto the ear surface, and a single-camera or multi-camera imaging system forming an image of the illuminated area. In the resulting 3D measurement system data processing can be performed locally (server at operator's location), remotely (remote server or in the cloud) or in a hybrid manner (combination of both local and remote processing).

The present invention provides the following advantages over the prior art, including a simpler, more comfortable apparatus that obviates the need for tracking targets on the patient's head, injection of silicon material in the ear or use of other consumables, disposable inflatable membrane, or the like.

In one aspect of the present invention, an ear scanner includes the following: a handpiece; an earpiece extending from the handpiece, wherein the earpiece has a distal end dimensioned and shaped to occupy an ear canal; a pattern projector configured to project a light pattern from said distal end; and one or more wide field-of-view (WFOV) imagers configured to capture, through said distal end, one or more images enabled by the light pattern.

In yet another aspect of the present invention, the ear scanner further includes wherein the pattern projector is configured to modulate the light pattern spatially, temporally or both; a user interface along an exterior surface of the handpiece, wherein the user interface is configured to enable one or more feedback modalities, wherein each feedback modality propagates a combination of visual, audible, and haptic output when said distal end of the earpiece is beyond a threshold distance from or within the ear canal, wherein the one or more WFOV imagers comprises a plurality of WFOV imagers wherein the WFOV of each WFOV imager of the plurality of WFOV imagers overlaps another WFOV thereof; and further including a WFOV flood illuminator configured to project a uniform intensity distribution of light from the distal end of the earpiece.

In another aspect of the present invention, a method of capturing and processing image data of a patient's ear includes the following: illuminating, via an earpiece dimensioned and shaped to occupy an ear canal of the patient's ear, a surface of the patient's ear with a light pattern; modulating the light pattern spatially or temporally or both; capturing a plurality of wide field-of-view (WFOV) images of the surface illuminated by the light pattern; and generating, by a processing unit, a three-dimensional image of said surface by combining the plurality of WFOV images based on the modulated light pattern.

These and other features, aspects and advantages of the present invention will become better understood with reference to the following drawings, description and claims.

DETAILED DESCRIPTION OF THE INVENTION

The following detailed description is of the best currently contemplated modes of carrying out exemplary embodiments of the invention. The description is not to be taken in a limiting sense but is made merely for the purpose of illustrating the general principles of the invention, since the scope of the invention is best defined by the appended claims.

Broadly, an embodiment of the present invention provides a method and apparatus for three-dimensional measurements of the outer ear shape, including the auditory canal and the concha.

Figure 1:
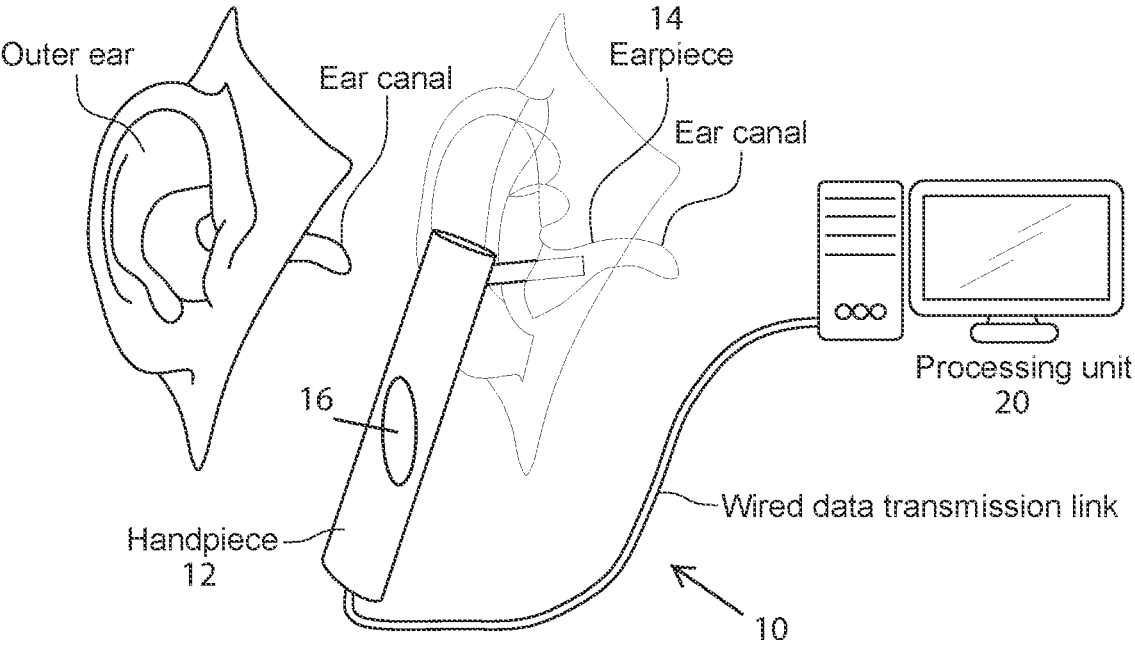
FIG. 1 is a schematic view of an exemplary embodiment of the present invention illustrating the systemic components: a handpiece, an earpiece, and a processing unit.

Referring to FIG. 1, the present invention may include a method and apparatus for three-dimensional measurements of the outer ear shape, including the auditory canal and the concha. The method embodies an ear scanner 10 having a compact handpiece 12 which is held by the operator and a digital processing unit 20 as depicted in FIG. 1.

The ear scanner 10 includes a handpiece 12 and an earpiece 14 extending from the handpiece 12. The ear scanner 10 further includes wide field-of-view single-imager or multi-imager architecture, pattern projector modulator, and flood illuminator capturing and projecting light from the earpiece 14. The handpiece 12 may provide a screen, touch-screen, or user interface 16 configured to provide additional visual, audio, or haptic feedback to the operator (expanded output) and/or to enrich control of the device by the operator (expanded input).

The earpiece 14 is dimensioned and shaped to be inserted deep into the auditory canal, typically the earpiece 14 is narrow and elongated. The earpiece 14 ends with a tip assembly featuring an electro-optical device for both illuminating and capturing imagery of parts of the ear surface. Handpiece 12 then transmits the captured data stream to the processing unit 20.

The digital processing unit 20 receives the data stream captured by the handpiece 12. The data is processed in real-time or near real-time and three-dimensional (3D) measurements of the outer ear shape are reconstructed, including the shape of the auditory canal. The processing unit 12 also allows the operator to visualize data that is captured or processed. Finally, the processing unit 20 is configured to export data that was captured or processed from the system.

The method of scanning the ear includes the following path. The operator holds the systemic handpiece 12 so that the earpiece 14 is facing the surface of the patient's ear, for instance the surface of the auditory canal or the concha or the auricle. The operator then moves the handpiece 12 (and thus earpiece 14) around the outer ear to view its surface under various orientations. During the operation of the device, ear surface data is captured continuously and transmitted to the processing unit 20.

The processing unit 20 processes the received data continuously and provides guidance to the operator in real-time. The guidance aims at assisting the operator when moving the earpiece 14 around the patient's ear. The guidance may include multiple feedback modalities: visual feedback, audio feedback and haptic feedback. For instance, the system will guide the operator should they move the earpiece 14 too far from the ear surface or should they position the earpiece 14 dangerously close to the patient's ear drum.

Figure 2:
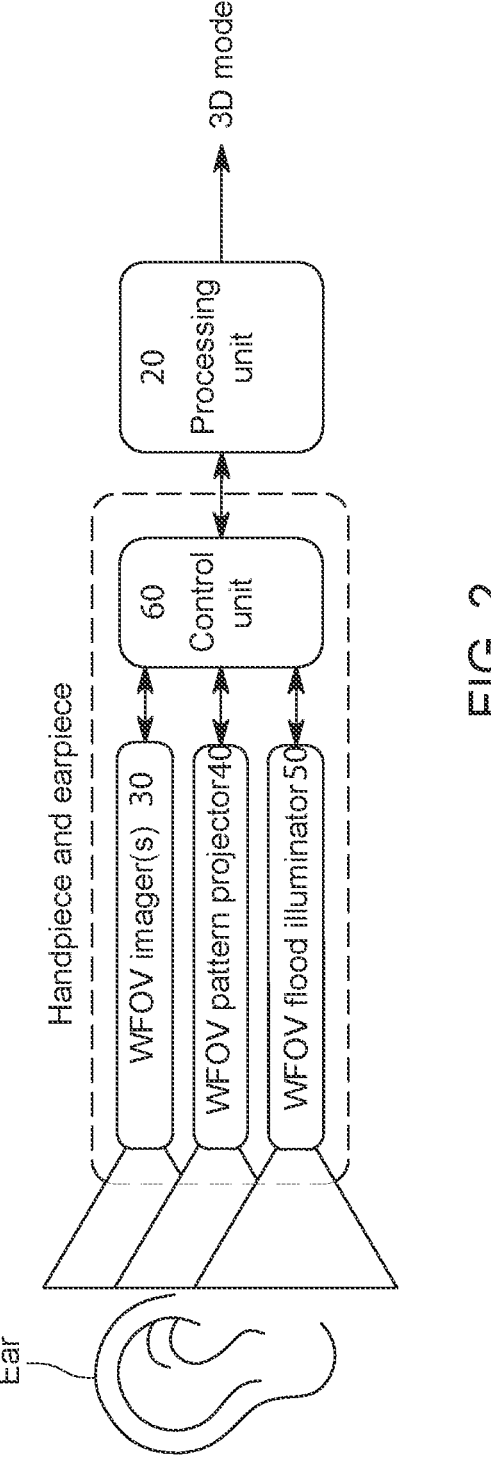
FIG. 2 is a schematic view of an exemplary embodiment of the present invention illustrating the functionality of the handpiece and the earpiece.

Referring to FIG. 2, the handpiece 12 and earpiece 14 include key functional components for capturing data:

One or more wide field-of-view (WFOV) imagers 30 to capture image streams of the ear surface. The WFOV imagers 30 may feature an optical WFOV objective 70. The WFOV imagers are designed and positioned so that their field-of-views overlap substantially. The WFOV imagers are configured to collect monochromatic or color images. Image capture is triggered by a control unit located in the handpiece 12. Imaging of the ear surface may be implemented using a single WFOV imager or multiple WFOV imagers depending on the 3D reconstruction approach selected.

A WFOV pattern projector 40 configured to project a light distribution with an engineered pattern onto the ear surface, wherein the engineered pattern can be spatially modulated (e.g., checkerboard pattern, stripes pattern, random pattern) or it can be temporally modulated, or it can be both. Like the WFOV imagers 30 the WFOV pattern projector 40 operates over a wide field-of-view. The projector light source can be a monochromatic source or broadband light source.

A WFOV flood illuminator may configured to illuminate the ear surface with a uniform intensity distribution over a wide field-of-view like the WFOV imagers 30. The WFOV flood illuminator may be one functionality of a light source 50.

A control unit 60 orchestrates the synchronization of the pattern projector 40, the flood illuminator, and the image capture using the imagers 30. The component also transmits the data captured to the processing unit 20.

Figure 3A:
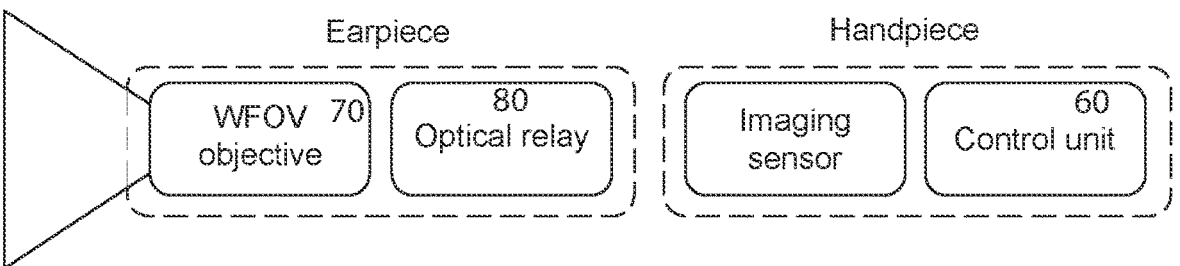
FIG. 3A is a schematic view of an exemplary embodiment of the present invention illustrating the functionality of a WFOV imager.

Referring to FIG. 3A, an optical WFOV objective 70 gathers the light from the ear surface over a wide field-of-view to form an image. The image is then relayed through the narrow earpiece 14 using an optical relay 80 onto an image sensor 90 located in the handpiece 12 along with the control unit 60.

Figure 3B:
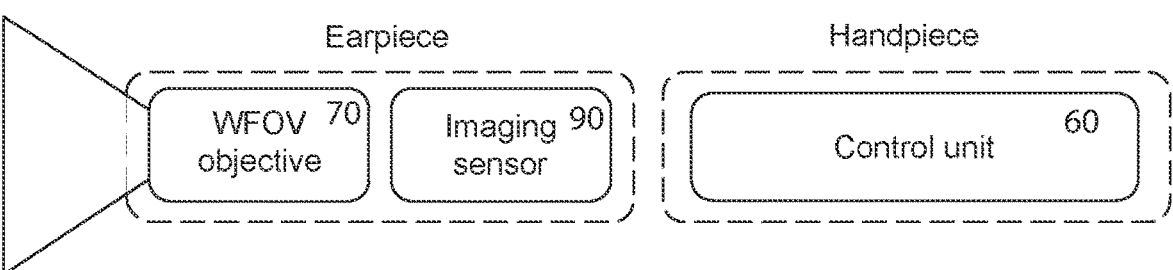
FIG. 3B is a schematic view of an exemplary embodiment of the present invention illustrating the functionality of a WFOV imager.

Alternatively, FIG. 3B depicts a so-called chip-in-tip architecture where the image formed by the WFOV objective 70 is captured using an image sensor 90 located inside the earpiece 14, right behind the objective 70. In this architecture the control unit remains in the handpiece. The image sensor can be implemented using a charge-coupled device (CCD) or a complementary metal-oxide-semiconductor (CMOS) chip.

Figure 4A:
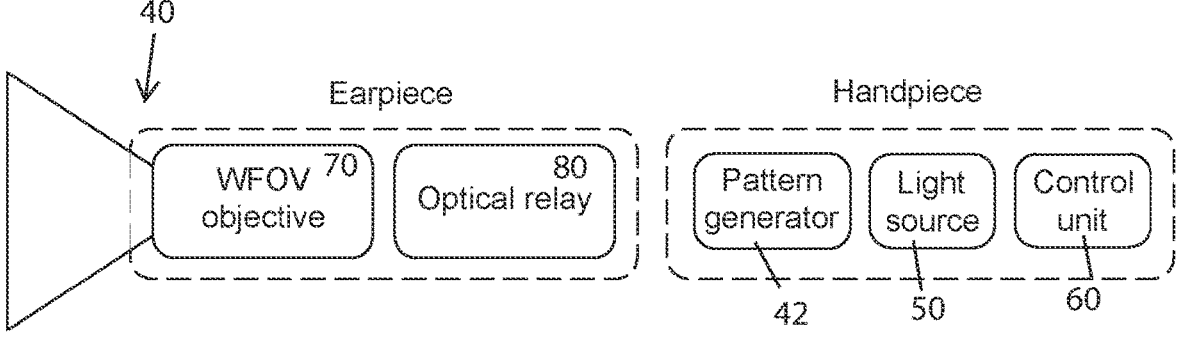
FIG. 4A is a schematic view of an exemplary embodiment of the present invention illustrating the functionality of a WFOV pattern projector.

Referring to FIG. 4A, the light source 50 for the pattern projector 40 is in the handpiece 12 of the ear scanner 10 as well as the pattern generator component 42 that generates a light field with a pattern distribution. The pattern generated is then relayed through the narrow earpiece 14 using an optical relay. This optical relay may be either the same as the one used for the WFOV imagers, or it can be a separate optical relay depending on the embodiment; thus, the present invention contemplates a plurality of optical relays. The optical objective component 42 then projects the pattern onto the ear surface over a WFOV.

Figure 4B:
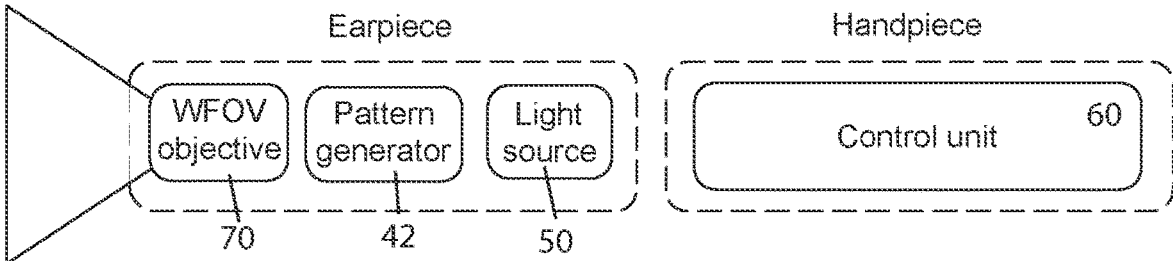
FIG. 4B is a schematic view of an exemplary embodiment of the present invention illustrating the functionality of a WFOV pattern projector.

In the pattern projector variation shown in FIG. 4B, the light source 50 may be inside the earpiece 14 as well as the pattern generator optics 42. Like in FIG. 4A, the WFOV objective 42 projects the pattern onto the ear surface. The light source 92 used in the pattern projector can include a laser source or a light-emitting diode (LED). Pattern generation can be achieved using an optical mask or a diffractive optics element (DOE) for instance.

Data Processing

Figure 5:
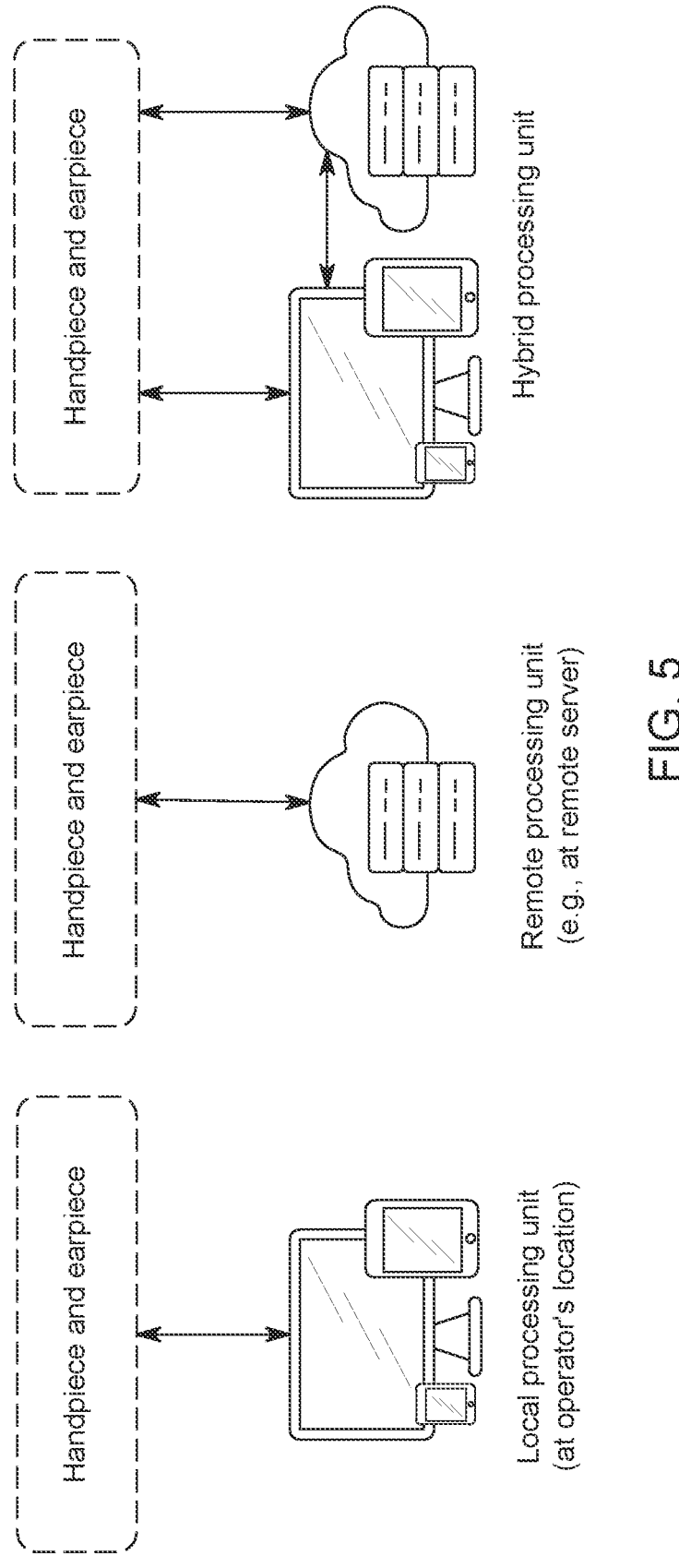
FIG. 5 is a schematic view of an exemplary embodiment of the present invention illustrating various implementations for processing data received from the handpiece.

The data stream from the handpiece is transmitted to a processing unit to generate 3D measurements of the ear shape, to provide visualization of the data and feedback to the operator and export the data. Data processing can be implemented in various manners: (a) data is processed at the operator's location (local processing shown on the left of FIG. 5), (b) data is processed remotely such as on a remote server or in the cloud (remote processing shown in the middle of FIG. 5), or data is processed using a combination of local and remote processing (hybrid processing shown on the right of FIG. 5).

As used in this application, the term "about" or "approximately" refers to a range of values within plus or minus 10% of the specified number. And the term "substantially" refers to up to 80% or more of an entirety. Recitation of ranges of values herein are not intended to be limiting, referring instead individually to any and all values falling within the range, unless otherwise indicated, and each separate value within such a range is incorporated into the specification as if it were individually recited herein.

For purposes of this disclosure, the term "aligned" means parallel, substantially parallel, or forming an angle of less than 35.0 degrees. For purposes of this disclosure, the term "transverse" means perpendicular, substantially perpendicular, or forming an angle between 55.0 and 125.0 degrees. Also, for purposes of this disclosure, the term "length" means the longest dimension of an object. Also, for purposes of this disclosure, the term "width" means the dimension of an object from side to side. For the purposes of this disclosure, the term "above" generally means superjacent, substantially superjacent, or higher than another object although not directly overlying the object. Further, for purposes of this disclosure, the term "mechanical communication" generally refers to components being in direct physical contact with each other or being in indirect physical contact with each other where movement of one component affect the position of the other.

The use of any and all examples, or exemplary language ("e.g.," "such as," or the like) provided herein, is intended merely to better illuminate the embodiments and does not pose a limitation on the scope of the embodiments or the claims. No language in the specification should be construed as indicating any unclaimed element as essential to the practice of the disclosed embodiments.

In the following description, it is understood that terms such as "first," "second," "top," "bottom," "up," "down," and the like, are words of convenience and are not to be construed as limiting terms unless specifically stated to the contrary.

It should be understood, of course, that the foregoing relates to exemplary embodiments of the invention and that modifications may be made without departing from the spirit and scope of the invention as set forth in the following claims.

What is claimed is:

1. An ear scanner comprising:
a handpiece;
an earpiece extending from the handpiece, wherein the earpiece has a distal end dimensioned and shaped to occupy an ear canal;
a pattern projector configured to project a light pattern from said distal end;
one or more wide field-of-view (WFOV) imagers configured to capture, through said distal end, one or more images enabled by the light pattern; and
a WFOV flood illuminator configured to project a uniform intensity distribution of light from the distal end of the earpiece.

2. The ear scanner of claim 1, wherein the pattern projector is configured to modulate the light pattern spatially and temporally.

3. The ear scanner of claim 1, further comprising a user interface along an exterior surface of the handpiece, wherein the user interface is configured to enable one or more feedback modalities.

4. The ear scanner of claim 3, wherein each feedback modality propagates a visual, audible, or haptic output when said distal end of the earpiece is beyond a threshold distance from or within the ear canal.

5. The ear scanner of claim 4, wherein the user interface includes a touchscreen enabling user input.

6. The ear scanner of claim 1, wherein the one or more WFOV imagers comprises a plurality of WFOV imagers wherein the WFOV of each WFOV imager of the plurality of WFOV imagers overlaps another WFOV thereof.

* * * * *